US011090296B2

(12) United States Patent
Okabe et al.

(10) Patent No.: US 11,090,296 B2
(45) Date of Patent: Aug. 17, 2021

(54) SUSTAINED-RELEASE PHARMACEUTICAL COMPOSITION

(71) Applicant: SANTEN PHARMACEUTICAL CO., LTD, Osaka (JP)

(72) Inventors: Komei Okabe, Ikoma (JP); Toyomi Fujisawa, Ikoma (JP); Kazuhito Yamada, Ikoma (JP)

(73) Assignee: SANTEN PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 15/558,260

(22) PCT Filed: Mar. 17, 2016

(86) PCT No.: PCT/JP2016/058455
§ 371 (c)(1),
(2) Date: Sep. 14, 2017

(87) PCT Pub. No.: WO2016/148228
PCT Pub. Date: Sep. 22, 2016

(65) Prior Publication Data
US 2018/0042907 A1 Feb. 15, 2018

(30) Foreign Application Priority Data

Mar. 18, 2015 (JP) .............................. JP2015-055196

(51) Int. Cl.
| *A61K 31/444* | (2006.01) |
| *A61K 9/00* | (2006.01) |
| *A61K 47/22* | (2006.01) |
| *A61K 47/10* | (2017.01) |
| *A61K 47/14* | (2017.01) |
| *A61K 47/20* | (2006.01) |
| *A61K 47/34* | (2017.01) |
| *A61P 27/02* | (2006.01) |

(52) U.S. Cl.
CPC .......... *A61K 31/444* (2013.01); *A61K 9/0002* (2013.01); *A61K 9/0048* (2013.01); *A61K 9/0051* (2013.01); *A61K 47/10* (2013.01); *A61K 47/14* (2013.01); *A61K 47/20* (2013.01); *A61K 47/22* (2013.01); *A61K 47/34* (2013.01)

(58) Field of Classification Search
CPC .. A61K 31/444; A61K 9/0051; A61K 9/0002; A61K 9/0048; A61K 47/22; A61K 47/10; A61K 47/14; A61K 47/20; A61K 47/34; A61P 27/02; Y10S 514/912
See application file for complete search history.

(56) References Cited

U.S. PATENT DOCUMENTS

| 4,001,388 | A | * | 1/1977 | Shell | ..................... | A61K 9/0048 424/438 |
| 5,980,945 | A | | 11/1999 | Ruiz | | |
| 9,029,398 | B2 | | 5/2015 | Niwa et al. | | |
| 9,359,328 | B2 | | 6/2016 | Niwa et al. | | |
| 9,546,140 | B2 | | 1/2017 | Niwa et al. | | |
| 9,902,698 | B2 | | 2/2018 | Niwa et al. | | |
| 10,668,011 | B2 | * | 6/2020 | Tamraz | ................... | A61K 47/14 |
| 10,682,340 | B2 | * | 6/2020 | Tamraz | ................ | A61K 9/0048 |
| 2005/0281879 | A1 | * | 12/2005 | Chen | ..................... | A61K 9/0024 424/486 |
| 2006/0073182 | A1 | | 4/2006 | Wong et al. | | |
| 2006/0210604 | A1 | | 9/2006 | Dadey et al. | | |
| 2007/0149574 | A1 | | 6/2007 | Honda et al. | | |
| 2007/0280992 | A1 | | 12/2007 | Margaron et al. | | |
| 2009/0074786 | A1 | | 3/2009 | Dor et al. | | |
| 2010/0227879 | A1 | * | 9/2010 | Mudumba | ............ | A61K 9/0048 514/291 |
| 2012/0116088 | A1 | | 5/2012 | Niwa et al. | | |
| 2014/0140992 | A1 | | 5/2014 | Wong et al. | | |
| 2015/0291560 | A1 | | 10/2015 | Niwa et al. | | |
| 2016/0251314 | A1 | | 9/2016 | Niwa et al. | | |
| 2017/0081286 | A1 | | 3/2017 | Niwa et al. | | |
| 2018/0000729 | A1 | * | 1/2018 | Tamraz | ................... | A61K 45/06 |
| 2018/0117016 | A1 | * | 5/2018 | Tamraz | ................ | A61K 9/0051 |

FOREIGN PATENT DOCUMENTS

| JP | 2008-514719 A | 5/2008 |
| JP | 2008-520547 A | 6/2008 |
| JP | 2010-536797 A | 12/2010 |
| WO | WO 2005/085201 A1 | 9/2005 |
| WO | WO 2008/143992 A2 | 11/2008 |
| WO | 2011/007870 A1 | 1/2011 |
| WO | 2013/036309 A2 | 3/2013 |
| WO | WO 2013/153559 A1 | 10/2013 |
| WO | WO 2015/041294 A1 | 3/2015 |

OTHER PUBLICATIONS

Evren Alğin Yapar, et al., "Effects of Solvent Combinations on Drug Release From Injectable Phase Sensitive Liquid Implants", Turk. J. Pharm. Sci., 2010, pp. 49-56, vol. 7, No. 1.
International Search Report (PCT/ISA/210) dated Jun. 21, 2016, by the Japanese Patent Office as the International Searching Authority for International Application No. PCT/JP2016/058455.
Written Opinion (PCT/ISA/237) dated Jun. 21, 2016, by the Japanese Patent Office as the International Searching Authority for International Application No. PCT/JP2016/058455.
Extended Search Report issued by the European Patent Office in corresponding European Patent Application No. 16765057.1-1109 dated Oct. 25, 2018 (7 pages).
Notice of Reasons for Refusal issued by the Japanese Patent Office in corresponding Japanese Patent Application No. 2016-053405 dated Nov. 19, 2019 (6 pages including partial English translation).

* cited by examiner

*Primary Examiner* — Abigail Vanhorn
(74) *Attorney, Agent, or Firm* — Buchanan, Ingersoll & Rooney PC

(57) ABSTRACT

The present invention relates to an ophthalmic depot preparation comprising benzyl benzoate and/or benzyl alcohol and polyethylene glycol and/or dimethylsulfoxide, wherein the volume ratio of benzyl benzoate and/or benzyl alcohol to polyethylene glycol and/or dimethylsulfoxide in the ophthalmic depot preparation is 75:25 to 25:75, and the total amount of benzyl benzoate and/or benzyl alcohol and polyethylene glycol and/or dimethylsulfoxide contained is 50% (w/w) or more.

16 Claims, 1 Drawing Sheet

Comparative Example 9    Example 28
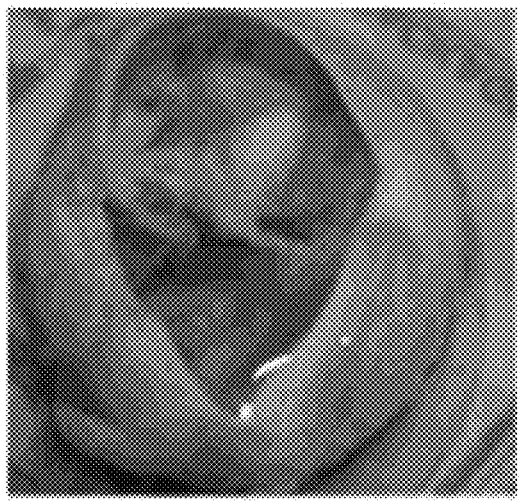 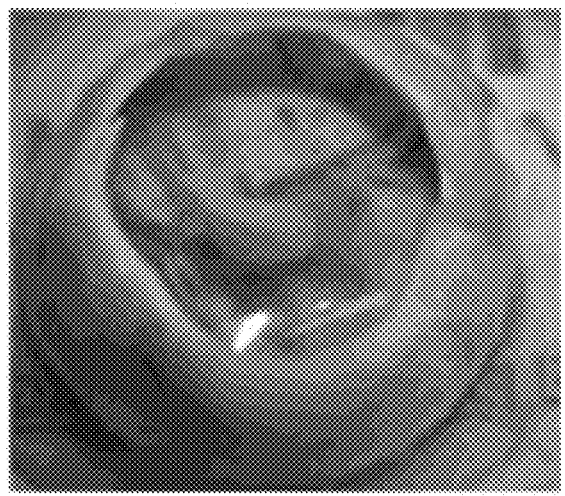

SUSTAINED-RELEASE PHARMACEUTICAL COMPOSITION

TECHNICAL FIELD

The present invention relates to an ophthalmic depot preparation comprising benzyl benzoate and/or benzyl alcohol, and polyethylene glycol and/or dimethylsulfoxide, wherein the volume ratio of benzyl benzoate and/or benzyl alcohol to polyethylene glycol and/or dimethylsulfoxide in the ophthalmic depot preparation is 75:25 to 25:75, and the total amount of benzyl benzoate and/or benzyl alcohol and polyethylene glycol and/or dimethylsulfoxide contained is 50% (w/w) or more.

The present invention relates to an ophthalmic depot preparation further containing a drug, and the drug is contained in the form of a compound represented by formula (1):

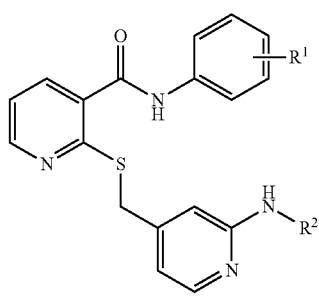

wherein $R^1$ represents a hydrogen atom, halogen atom, hydroxyl group, $C_{1-6}$ alkyl group, $C_{1-6}$ alkyl group substituted with one or more halogen atoms, $C_{1-6}$ alkoxy group, or $C_{1-6}$ alkoxy group substituted with one or more halogen atoms, and $R^2$ represents a hydrogen atom, $C_{1-6}$ alkyl group, $C_{1-6}$ alkylcarbonyl group, or $C_{1-6}$ alkylcarbonyl group substituted with one or more hydroxyl groups, or a salt thereof.

BACKGROUND ART

For example, an invasive pharmaceutical agent such as an intravitreal injection preparation is preferably a preparation in which a drug is gradually released from an injected site after having been administered into the body and subsequently demonstrates a pharmacological effect over a long period of time from the viewpoint of reducing the burden on the patient resulting from administration of the pharmaceutical agent. A known means for realizing this is a preparation in which a depot is formed at a site where a pharmaceutical agent is injected and a drug is gradually released from that site.

Non-Patent Document 1 discloses an in situ forming implant that contains poly(lactic-co-glycolic acid) (PLGA), and benzyl benzoate, benzyl alcohol, PEG400, DMSO or a mixture thereof as a solvent, and granisetron hydrochloride as a drug, and describes an examination of the release of the granisetron hydrochloride in a phosphate buffer. However, Non-Patent Document 1 does not describe an in situ forming implant that does not contain poly(lactic co-glycolic acid) (PLGA), and the use of the in situ forming implant described in Non-Patent Document 1 in the field of ophthalmology is also not described.

Patent Document 1 discloses a preparation that contains PLGA, and sucrose acetate isobutyrate (SAIB), and further benzyl benzoate, benzyl alcohol, DMSO or a mixture thereof. However, although Patent Document 1 describes a depot preparation, it does not describe a depot preparation that does not contain PLGA and SAIB, and the use of the depot preparation in field of ophthalmology is not described or suggested.

Patent Document 2 discloses a sustained-release preparation for intramuscular administration that contains DMSO as a solvent, caprylic/capric triglyceride (Myglyol 812) as an oily mixture, and benzyl benzoate, benzyl alcohol or a mixture thereof as a sustained-release component, and a fulvestrant as a drug. However, Patent Document 2 does not describe a sustained-release preparation that does not contain Myglycol 812, and the use of that sustained-release preparation in the field of ophthalmology is also not described.

These documents do not describe an ophthalmic depot preparation containing benzyl benzoate and/or benzyl alcohol and polyethylene glycol and/or dimethylsulfoxide, wherein the volume ratio of benzyl benzoate and/or benzyl alcohol to polyethylene glycol and/or dimethylsulfoxide in the ophthalmic depot preparation is 75:25 to 25:75, and the total amount of benzyl benzoate and/or benzyl alcohol and polyethylene glycol and/or dimethylsulfoxide contained is 50% (w/w) or more. In addition, it is also not described that the ophthalmic depot preparation demonstrates a pharmacological effect over a long period of time by gradually releasing a drug by forming similar depots regardless of the administration site or conditions around that site.

PRIOR ART DOCUMENTS

Patent Documents

[Patent Document 1] International Publication No. WO 2008/143992

[Patent Document 2] International Publication No. WO 2013/153559

Non-Patent Documents

[Non-Patent Document 1] Turk. J. Pharm. Sci., 7(1), 2010, 49-56

SUMMARY OF INVENTION

Technical Problem

A depot preparation is a preparation which, after administration into a body, forms a depot containing a drug and continuously releases the drug. In some cases, the formed depot has a randomly unstable shape. Even in such a case, the preparation may be used for continuously releasing the drug. However, in order to more stably achieve sustained release properties, it is preferred that the formed depot has a spherically stable shape. Further, the inventors of the present invention found that in a preparation in which a pharmaceutical agent forms a depot, the shape of the depot formed differently depending on the difference in administration site or conditions around that site (such as in the vitreous body and in the anterior chamber, or conditions around them), and that the preparation might have no sustained release properties when administered into a certain site. An object of the present invention is to provide an ophthalmic depot preparation that gradually releases a drug after having been administered into the body, the ophthalmic depot preparation being capable of similarly forming a depot regardless of the administration site or conditions around that site and stably achieving sustained release of the drug.

Solution to Problem

As a result of extensive studies on solvents that dissolve drugs in order to solve the aforementioned problems, the inventors of the present invention found that, an ophthalmic depot preparation containing benzyl benzoate and/or benzyl alcohol and polyethylene glycol and/or dimethylsulfoxide, wherein the volume ratio of benzyl benzoate and/or benzyl alcohol to polyethylene glycol and/or dimethylsulfoxide in the ophthalmic depot preparation is 75:25 to 25:75, and the total amount of benzyl benzoate and/or benzyl alcohol and polyethylene glycol and/or dimethylsulfoxide contained is 50% (w/w) or more, gradually releases a drug by forming similar depots regardless of the administration site or conditions around that site, thereby leading to completion of the present invention.

Namely, the present invention relates to that indicated below.

(1) An ophthalmic depot preparation containing benzyl benzoate and/or benzyl alcohol and polyethylene glycol and/or dimethylsulfoxide, wherein
the volume ratio of benzyl benzoate and/or benzyl alcohol to polyethylene glycol and/or dimethylsulfoxide in the ophthalmic depot preparation is 75:25 to 25:75, and
the total amount of benzyl benzoate and/or benzyl alcohol and polyethylene glycol and/or dimethylsulfoxide contained is 50% (w/w) or more.

(2) The ophthalmic depot preparation described in (1) above, further containing a drug.

(3) The ophthalmic depot preparation described in (2) above, wherein the drug is a compound represented by formula (1):

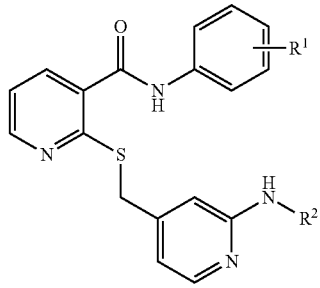

(1)

wherein,
$R^1$ represents a hydrogen atom, halogen atom, hydroxyl group, $C_{1-6}$ alkyl group, $C_{1-6}$ alkyl group substituted with one or more halogen atoms, $C_{1-6}$ alkoxy group, or $C_{1-6}$ alkoxy group substituted with one or more halogen atoms, and
$R^2$ represents a hydrogen atom, $C_{1-6}$ alkyl group, $C_{1-6}$ alkylcarbonyl group, or $C_{1-6}$ alkylcarbonyl group substituted with one or more hydroxyl groups, or a salt thereof.

(4) The ophthalmic depot preparation described in (3) above, wherein in the formula (1)
$R^1$ represents a $C_{1-6}$ alkoxy group or $C_{1-6}$ alkoxy group substituted with one or more halogen atoms, and
$R^2$ represents a $C_{1-6}$ alkylcarbonyl group or $C_{1-6}$ alkylcarbonyl group substituted with one or more hydroxyl groups.

(5) The ophthalmic depot preparation described in (3) above, wherein in the formula (1)
$R^1$ represents a $C_{1-6}$ alkoxy group substituted with one or more halogen atoms, and
$R^2$ represents a $C_{1-6}$ alkylcarbonyl group substituted with one or more hydroxyl groups.

(6) The ophthalmic depot preparation described in (3) above, wherein the compound represented by formula (1) is 2-[[[2-[(hydroxyacetyl)amino]-4-pyridinyl]methyl]thio]-N-[4-(trifluoromethoxy)phenyl]-3-pyridinecarboxamide or a salt thereof.

(7) The ophthalmic depot preparation described in any one of (1) to (6) above, wherein the average molecular weight of the polyethylene glycol is within the range of 90 to 2,200.

(8) The ophthalmic depot preparation described in any one of (1) to (7) above, wherein the polyethylene glycol is a polyethylene glycol selected from the group consisting of PEG400, PEG600, PEG800 and PEG1,000.

(9) The ophthalmic depot preparation described in any one of (1) to (8) above, wherein the volume ratio of benzyl benzoate and/or benzyl alcohol to polyethylene glycol and/or dimethylsulfoxide is 60:40 to 35:65.

(10) The ophthalmic depot preparation described in any one of (1) to (8) above, wherein the volume ratio of benzyl benzoate and/or benzyl alcohol to polyethylene glycol and/or dimethylsulfoxide is 50:50 to 40:60.

(11) The ophthalmic depot preparation described in any one of (1) to (10) above, wherein the total amount of benzyl benzoate and/or benzyl alcohol and polyethylene glycol and/or dimethylsulfoxide contained is 80% (w/w) or more.

(12) The ophthalmic depot preparation described in any one of (1) to (11) above, wherein the total amount of benzyl benzoate and/or benzyl alcohol contained is 25% (w/w) to 60% (w/w).

(13) The ophthalmic depot preparation described in any one of (1) to (12) above, wherein the total amount of polyethylene glycol and/or dimethylsulfoxide contained is 30% (w/w) to 62% (w/w).

(14) The ophthalmic depot preparation described in any one of (2) to (13) above, which further comprises tocopherol or derivatives thereof.

(15) The ophthalmic depot preparation described in (14) above, wherein the amount of tocopherol or derivatives thereof contained is 0.001% (w/v) to 10% (w/v).

(16) The ophthalmic depot preparation described in any one of (1) to (15) above, which is for administration into the vitreous body or anterior chamber.

(17) The ophthalmic depot preparation described in any one of (2) to (16) above, wherein the drug is contained at 0.001% (w/v) to 30% (w/v).

(18) The ophthalmic depot preparation described in any one of (2) to (17) above, which is for prevention and/or treatment of an eye disease.

(19) The ophthalmic depot preparation described in any one of (1) to (18) above, which does not contain poly(lactic-co-glycolic acid) (PLGA).

(20) The ophthalmic depot preparation described in (1) to (19) above, which does not contain a medium-chain triglyceride.

(21) The ophthalmic depot preparation described in any one of (1) to (20) above, which does not contain sucrose acetate isobutyrate (SAIB).

(22) The ophthalmic depot preparation described in any one of (2) to (21) above, which substantially only contains a drug, benzyl benzoate, polyethylene glycol and tocopherol or derivatives thereof.

(23) The ophthalmic depot preparation described in any one of (2) to (21) above, which substantially only contains a drug, benzyl benzoate, dimethylsulfoxide and tocopherol or derivatives thereof.

(24) The ophthalmic depot preparation described in any one of (2) to (21) above, which substantially only contains a drug, benzyl benzoate and polyethylene glycol.

(25) The ophthalmic depot preparation described in any one of (2) to (21) above, which substantially only contains a drug, benzyl benzoate and dimethylsulfoxide.

(26) The ophthalmic depot preparation described in (16) above, wherein the eye disease is age-related macular degeneration, diabetic retinopathy, retinopathy of prematurity, retinal vein occlusion, retinal artery occlusion, polypoidal choroidal vasculopathy, retinal angiomatous proliferation, myopic choroidal neovascularization, diabetic macular edema, ocular tumor, radiation retinopathy, rubeosis iridis, neovascular glaucoma or proliferative vitreoretinopathy (PVR), primary open-angle glaucoma, secondary open-angle glaucoma, normal tension glaucoma, hypersecretion glaucoma, primary closed-angle glaucoma, secondary closed-angle glaucoma, plateau iris glaucoma, combined mechanism glaucoma, developmental glaucoma, corticosteroid glaucoma, exfoliation glaucoma, amyloidotic glaucoma, neovascular glaucoma, malignant glaucoma, capsular glaucoma, plateau iris syndrome or high tension glaucoma.

(27) The ophthalmic depot preparation described in any one of (1) to (26) above, wherein 1 μL to 1,000 μL is administered at one time.

(28) The ophthalmic depot preparation described in any one of (1) to (27) above, which is administered at an interval of once a week to once every three years.

(29) The ophthalmic depot preparation described in any one of (1) to (28) above, which is for sustained drug release.

(30) The ophthalmic depot preparation according to any one of (1) to (29) above, which is contained in a syringe made of glass, cycloolefin polymer, polyolefin or polycarbonate.

(31) The ophthalmic depot preparation according to any one of (1) to (29) above, which is contained in a syringe made of glass, cycloolefin polymer or polypropylene.

(32) A method in which a drug contained in an ophthalmic depot preparation is stabilized by incorporating tocopherol or derivatives thereof in said ophthalmic depot preparation,
said ophthalmic depot preparation comprising:
benzyl benzoate and/or benzyl alcohol, and
polyethylene glycol and/or dimethylsulfoxide, wherein,
the volume ratio of benzyl benzoate and/or benzyl alcohol to polyethylene glycol and/or dimethylsulfoxide in the ophthalmic depot preparation is 75:25 to 25:75, and
the total amount of benzyl benzoate and/or benzyl alcohol and polyethylene glycol and/or dimethylsulfoxide contained is 50% (w/w) or more.

Furthermore, each of the configurations of (1) to (32) above can be combined by arbitrarily selecting two or more configurations.

Advantageous Effects of Invention

The ophthalmic depot preparation of the present invention is an ophthalmic depot preparation that gradually releases a drug after being administered into the body, and demonstrates a pharmacological effect over a long period of time by gradually and stably releasing the drug by forming similar depots regardless of the administration site or conditions around that site. Moreover, the ophthalmic depot preparation of the present invention has adequate safety as a pharmaceutical.

BRIEF DESCRIPTION OF DRAWING

The FIGURE provides photographs showing the shapes of depos formed by the ophthalmic depot preparation of the present invention administered into the vitreous body of a rabbit.

DESCRIPTION OF EMBODIMENTS

The following provides a detailed explanation of the present invention.

With respect to the ophthalmic depot preparation of the present invention, a depot preparation is a preparation for continuously releasing a drug, which preparation forms depot (mass) after the administration into a body or the like. There is no particular limitation with respect to the status of the depot preparation and the preparation may be in a dissolved state or suspended state, but it is preferred that the preparation is in a dissolved state.

There are no particular limitations on the drug contained in the ophthalmic depot preparation of the present invention, and specific examples thereof include tyrosine kinase inhibitors such as Tafetinib, SIM-817378, ACTB-1003, Chiauranib, CT-53608, Cinnamon, chim4G8-SDIE, CEP-5214, IMC-1C11, CEP-7055, 3-[5-[2-[N-(2-Methoxyethyl)-N-methylamino]ethoxy]-1H-indol-2-yl]quinolin-2(1H)-one, hF4-3C5, ZK-CDK, IMC-EB10, LS-104, CYC-116, OSI-930, PF-337210, JNJ-26483327, SSR-106462, R-1530, PRS-050, TG-02, SC-71710, SB-1578, AMG-191, AMG-820, Sulfatinib, Lucitanib hydrochloride, JNJ-28312141, Ilorasertib, PLX-5622, ARRY-382, TAS-115, Tanibirumab, Henatanib, LY-2457546, PLX-7486, FPA-008, NVP-AEE-788, cgi-1842, RAF-265, MK-2461, SG-00529, Rebastinib, Golvatinib, Roniciclib, BVT-II, X-82, XV-615, KD-020, Lestaurtinib, Delphinidin, Semaxanib, Vatalanib, OSI-632, Telatinib, Alacizumab pegol, ATN-224, Tivozanib, XL-999, Icrucumab, Foretinib, Crenolanib besylate, R-406, Brivanib, Pegdinetanib, TG-100572, Olaratumab, Fostamatinib disodium, BMS-690514, AT-9283, MGCD-265, Quizartinib, ENMD-981693, Famitinib, Anlotinib, Tovetumab, PLX-3397, Fruquintinib, (−)-Epigallocatechin, Midostaurin, NSC-706456, Orantinib, Cediranib, Dovitinib, XL-647, Motesanib, Linifanib, Brivanib, Cediranib, Apatinib, Fedratinib, Pacritinib, Ramucirumab, Intedanib, Masitinib, Elemene, Dihydroartemisinin, WS-1442, Itraconazole, Leflunomide, Dihydroartemisinin, Imatinib, Sorafenib, Sunitinib, Dasatinib, Pazopanib, Vandetanib, Axitinib, Regoarfenib, Caboazantinib and Ponatinib, steroids such as hydrocortisone, triamcinolone, fluocinolone, dexamethasone and betamethasone, prostaglandin derivatives such as isopropyl unoprostone, latanoprost, bimatoprost and travoprost, immunosuppressants such as cyclosporine, sirolimus and FK506, antiallergic drugs such as azelastine, non-steroidal anti-inflammatory drugs such as indomethacin, bromfenac and diclofenac, angiogenesis inhibitors such as pazopanib, SU5416, lapatanib, ranibizumab and bevacizumab, circulation ameliorants such as nicardipine and nitrendipine, antioxidants such as vitamin E, carbonic anhydrase inhibitors such as acetazolamide and brinzolamide, β-receptor blockers such as timolol and carteolol, visual cycle modulators such as vitamin A derivatives, neurotrophic factors such as ciliary neurotropic factor (CNTF) and brain-derived neurotrophic factor (BDNF), growth factors such as nerve growth factor (NGF) and hepatocyte growth factor (HGF), aptomers such as pegaptinib, nucleic acid pharmaceuticals such as various types of antisense nucleic acids and siRNA, antibody or peptide preparations such as lucentis, endoglin antibody and IgG, VEGF inhibitors such as those described in Japanese Unexamined Patent Publication No. 2006-96739, 2011-37844, 2005-232149, 2006-273851, 2006-306861 and 2008-266294, compounds having glucocorticoid receptor binding activity such as those described in Japanese Unexamined Patent Publication No. 2007-230993, 2008-074829, 2008-143889, 2008-143890, 2008-143891, 2009-007344 and 2009-084274, selective glucocorticoid receptor antagonists such as RU24858, anti-cancer agents such as fluorouracil, Janus kinase inhibitors such as tofacitinib, and protein kinase inhibitors such as ruboxistaurin mesylate.

Preferable specific examples of drugs contained in the ophthalmic depot preparation of the present invention include compounds represented by the aforementioned formula (1) and salts thereof.

A "halogen atom" refers to fluorine, chlorine, bromine or iodine.

A "$C_{1-6}$ alkyl group" refers to a linear or branched alkyl group having 1 to 6 carbon atoms, and is preferably a linear or branched alkyl group having 1 to 4 carbon atoms. Specific examples include a methyl group, ethyl group, n-propyl group, n-butyl group, n-pentyl group, n-hexyl group, isopropyl group, isobutyl group, sec-butyl group, tert-butyl group and isopentyl group.

A "$C_{1-6}$ alkoxy group" refers to a group in which the hydrogen atom of a hydroxyl group is substituted with the aforementioned $C_{1-6}$ alkyl group. Specific examples include a methoxy group, ethoxy group, n-propoxy group, n-butoxy group, n-pentoxy group, n-hexyloxy group, isopropoxy group, isobutoxy group, sec-butoxy group, tert-butoxy group and isopentyloxy group.

A "$C_{1-6}$ alkylcarbonyl group" refers to a group in which the hydrogen atom of a formyl group is substituted with the aforementioned $C_{1-6}$ alkyl group. Specific examples include a methylcarbonyl group (acetyl group), ethylcarbonyl group, n-propylcarbonyl group, n-butylcarbonyl group, n-pentylcarbonyl group, n-hexylcarbonyl group, isopropylcarbonyl group, isobutylcarbonyl group, sec-butylcarbonyl group, tert-butylcarbonyl group and isopentylcarbonyl group.

The phrase "substituted with one or more halogen atoms" as stated in the present invention refers to the aforementioned $C_{1-6}$ alkyl group being substituted with one to the maximum substitutable number of halogen atoms. Each halogen atom may be the same or different, the case in which the number of halogen atoms is 2 or 3 is preferable, and the case in which the number of halogen atoms is 3 is particularly preferable.

The phrase "substituted with one or more hydroxyl groups" as stated in the present invention refers to the aforementioned $C_{1-6}$ alkyl group being substituted with one to the maximum possible substitutable number of hydroxyl groups. The case in which the number of hydroxyl groups is 1 or 2 is preferable, and the case in which the number of hydroxyl groups is 1 is particularly preferable.

In addition, the drug in the present invention includes derivatives such as esters and amides. Specific examples of esters include esters in which a carboxylic acid such as acetic acid, propionic acid, isopropionic acid, butyric acid, isobutyric acid and pivalic acid is condensed with a hydroxyl group in the drug. Specific examples of amides include amides in which a carboxylic group such as acetic acid, propionic acid, isopropionic acid, butyric acid, isobutyric acid and pivalic acid is condensed with an amino group in the drug.

In addition, the contained drug may be in the form of a hydrate or solvate.

In the case the contained drug has geometric isomers, tautomers or optical isomers, these isomers are also included within the scope of the present invention.

Moreover, in the case the contained drug has crystal polymorphism, crystal polymorphs are also included within the scope of the present invention.

(a) Preferable examples of compounds represented by formula (1) include compounds, or salts thereof, in which each group is the group indicated below:

(a1) $R^1$ represents a $C_{1-6}$ alkoxy group or $C_{1-6}$ alkoxy group substituted with one or more halogen atoms; and/or (a2) $R^2$ represents a $C_{1-6}$ alkylcarbonyl group or $C_{1-6}$ alkylcarbonyl group substituted with one or more hydroxyl groups.

Namely, in compounds represented by formula (1), preferable examples thereof include compounds, or salts thereof, composed of one or two or more of each of the combinations selected from the aforementioned (a1) and (a2).

(b) More preferable examples of compounds represented by formula (1) include compounds, or salts thereof, in which each group is the group indicated below:

(b1) $R^1$ represents a $C_{1-6}$ alkoxy group substituted with one or more halogen atoms; and/or (b2) $R^2$ represents a $C_{1-6}$ alkylcarbonyl group substituted with one or more hydroxyl groups.

Namely, in compounds represented by formula (1), preferable examples thereof include compounds, or salts thereof, composed of one or two or more of each of the combinations selected from the aforementioned (b 1) and (b2). In addition, the conditions for selection thereof can be combined with the conditions of (a).

(c) The most preferable example of compounds represented by formula (1) is the compound (2-[[[2-[(hydroxyacetyl)amino]-4-pyridinyl]methyl]thio]-N-[4-(trifluoromethoxy)phenyl]-3-pyridinecarboxamide), or a salt thereof, represented by formula (2).

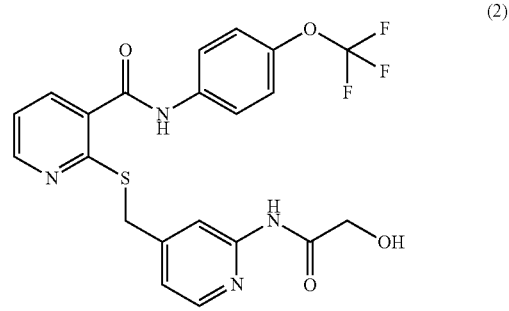 [SMILES: O=C(CO)Nc1cc(CSc2ncccc2C(=O)Nc2ccc(OC(F)(F)F)cc2)ccn1]

(2)

The compound represented by formula (1), or a salt thereof, contained in the ophthalmic depot preparation of the present invention can be produced according to an ordinary method in the relevant technical field, such as the method described in U.S. Unexamined Patent Application Publication No. 2007/0149574.

In the ophthalmic depot preparation of the present invention, the contained drug may be a salt, and there are no particular limitations thereon provided it is allowed as a pharmaceutical. Examples of salts include salts of inorganic acids, salts of organic acids, quaternary ammonium salts, salts with halogen ions, salts with alkaline metals, salts with alkaline earth metals, metal salts and salts with organic amines. Examples of salts of inorganic acids include salts with hydrochloric acid, hydrobromic acid, hydroiodic acid, nitric acid, sulfuric acid and phosphoric acid. Examples of salts of organic acids include salts with acetic acid, oxalic acid, fumaric acid, maleic acid, succinic acid, malic acid, citric acid, tartaric acid, adipic acid, gluconic acid, glucoheptonic acid, glucuronic acid, terephthalic acid, methanesulfonic acid, alanine, lactic acid, hippuric acid, 1,2-ethanedisulfonic acid, isethionic acid, lactobionic acid, oleic acid, gallic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalenesulfonic acid and sulfosalicylic acid. Examples of quaternary ammonium salts include salts with methyl bromate and methyl iodate. Examples of salts with halogen ions include salts with chloride ions, bromide ions and iodide ions, examples of salts with alkaline metals include lithium, sodium and potassium salts, examples of salts with alkaline earth metals include calcium and magnesium salts, and examples of metal salts include iron and zinc salts. Examples of salts of organic amines include salts with triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine and N,N-bis(phenylmethyl)-1,2-ethanediamine.

In the ophthalmic depot preparation of the present invention, although there are no particular limitations on the content of the contained drug provided it is an adequate amount for demonstrating a desired pharmacological effect, it is preferably 0.001% (w/v) to 30% (w/v), more preferably 0.01% (w/v) to 25% (w/v), even more preferably 0.1% (w/v) to 20% (w/v), still more preferably 0.5% (w/v) to 15% (w/v), particularly preferably 1% (w/v) to 12% (w/v), and most preferably 1% (w/v), 1.5% (w/v), 2% (w/v), 2.5% (w/v), 3% (w/v), 3.5% (w/v), 4% (w/v), 5% (w/v), 6% (w/v), 7% (w/v), 8% (w/v), 9% (w/v), 10% (w/v), 11% (w/v) or 12% (w/v). % (w/v) denotes the mass (g) of the component (i.e., the drug in this paragraph) in 100 mL of the ophthalmic depot preparation of the present invention. The same is applied unless otherwise particularly specified.

The benzyl benzoate contained in the ophthalmic depot preparation of the present invention is a compound represented by the chemical formula: $PhCO_2CH_2Ph$.

The benzyl alcohol contained in the ophthalmic depot preparation of the present invention is a compound represented by the chemical formula: $PhCH_2OH$.

In the ophthalmic depot preparation of the present invention, the content of benzyl benzoate and/or benzyl alcohol is preferably 15% (w/w) to 75% (w/w), more preferably 20% (w/w) to 70% (w/w), even more preferably 25% (w/w) to 60% (w/w), even still more preferably 27% (w/w) to 55% (w/w), particularly preferably 30% (w/w) to 50% (w/w) and most preferably 35% (w/w) to 48% (w/w). % (w/v) denotes the mass (g) of the component (i.e., benzyl benzoate and/or benzyl alcohol in this paragraph) in 100 g of the ophthalmic depot preparation of the present invention. The same is applied unless otherwise particularly specified.

The polyethylene glycol (PEG) contained in the ophthalmic depot preparation of the present invention is a polyether obtained by polymerizing ethylene glycol, is represented by the general formula: $HO(CH_2CH_2O)_nH$, and n represents the degree of polymerization. A commercially available product or that produced in accordance with an ordinary method in the relevant technical field can be used for the polyethylene glycol (PEG).

In the ophthalmic depot preparation of the present invention, the average molecular weight of the polyethylene glycol is preferably 90 to 2,200, more preferably 100 to 2,000, even more preferably 150 to 1,500, further more preferably 200 to 1,300, particularly preferably 300 to 1,200, more particularly 360 to 1,100 and most preferably 400 to 1,000. Specific examples of the polyethylene glycol include PEG100, PEG200, PEG300, PEG400, PEG600, PEG800 and PEG1,000.

In the ophthalmic depot preparation of the present invention, the content of the polyethylene glycol is preferably 15% (w/w) to 75% (w/w), more preferably 20% (w/w) to 70% (w/w), even more preferably 30% (w/w) to 62% (w/w), particularly preferably 40% (w/w) to 60% (w/w) and most preferably 43% (w/w) to 57% (w/w).

The dimethylsulfoxide (DMSO) contained in the ophthalmic depot preparation of the present invention is a compound represented by the chemical formula: $CH_3SOCH_3$.

In the ophthalmic depot preparation of the present invention, the content of the dimethylsulfoxide is preferably 15% (w/w) to 75% (w/w), more preferably 20% (w/w) to 70% (w/w), even more preferably 30% (w/w) to 62% (w/w), particularly preferably 40% (w/w) to 60% (w/w) and most preferably 43% (w/w) to 57% (w/w).

The total weight of the benzyl benzoate and/or benzyl alcohol and polyethylene glycol and/or dimethylsulfoxide contained in the ophthalmic depot preparation of the present invention is 50% (w/w) or more and preferably 80% (w/w) or more of the total weight of the ophthalmic depot preparation. In addition, the total weight of the benzyl benzoate and/or benzyl alcohol and polyethylene glycol and/or dimethylsulfoxide contained in the ophthalmic depot preparation of the present invention is preferably 60% (w/w) to 99.99% (w/w), more preferably 70% (w/w) to 99.99% (w/w), even more preferably 80% (w/w) to 99.5% (w/w), particularly preferably 85% (w/w) to 99.3% (w/w) and most preferably 90% (w/w) to 99% (w/w).

The volume ratio of the benzyl benzoate and/or benzyl alcohol to polyethylene glycol and/or dimethylsulfoxide contained in the ophthalmic depot preparation of the present invention is 75:25 to 25:75, preferably 60:40 to 35:65, more preferably 50:50 to 40:60 and most preferably 45:55 to 40:60. Furthermore, volume is calculated with the volume of benzyl benzoate and/or benzyl alcohol and polyethylene glycol and/or dimethylsulfoxide at 25° C. and 1 atm.

An additive can be used as necessary in the ophthalmic depot preparation of the present invention.

When additives are incorporated into the ophthalmic depot preparation of the present invention, the amounts of the additives can be appropriately adjusted depending on the types or the like of the additives, and the total amount of the additives is preferably 0.0001% (w/v) to 30% (w/v), more preferably 0.001% (w/v) to 25% (w/v), still more preferably 0.01% (w/v) to 20% (w/v), particularly preferably 0.1% (w/v) to 15% (w/v) and most preferably 1% (w/v) to 10% (w/v).

To the ophthalmic depot preparation of the present invention, as additives which can be used for pharmaceuticals, for example, surfactants, buffering agents, tonicity agents, stabilizers, preservatives, antioxidants, high molecular weight polymers and solvents can be added, if necessary.

Examples of surfactants able to be used as pharmaceutical additives that can be incorporated in the ophthalmic depot preparation of the present invention include cationic surfactants, anionic surfactants and nonionic surfactants. Examples of anionic surfactants include phospholipids, and examples of phospholipids include lecithin. Examples of cationic surfactants include alkylamine salts, alkylamine polyoxyethylene adducts, fatty acid triethanolamine monoester salts, acylaminoethyl diethylamine salts, fatty acid polyamine condensates, alkyltrimethylammonium salts, dialkyldimethylammonium salts, alkyldimethylbenzylammonium salts, alkylpyridinium salts, acylaminoalkyl ammonium salts, acylaminoalkyl pyridinium salts, diacyloxyethylammonium salts, alkylimidazolines, 1-acylaminoethyl-2-alkylimidazolines and 1-hydroxyethyl-2-alkylimidazolines. Examples of alkyldimethylbenzylammonium salts include benzalkonium chloride and cetalkonium chloride. Examples of nonionic surfactants include polyoxyethylene fatty acid esters, polyoxyethylene sorbitan fatty acid esters, polyoxyethylene hydrogenated castor oil, polyoxyethylene castor oil, polyoxyethylene polyoxypropylene glycol, sucrose fatty acid esters and vitamin E-TPGS.

Examples of polyoxyethylene fatty acid esters include Polyoxyl 40 stearate.

Examples of polyoxyethylene sorbitan fatty acid esters include Polysorbate 80, Polysorbate 60, Polysorbate 40, polyoxyethylene sorbitan monolaurate, polyoxyethylene sorbitan trioleate and Polysorbate 65.

Various polyoxyethylene hydrogenated castor oils having different degrees of polymerization of ethylene oxide can be used for the polyoxyethylene hydrogenated castor oil, and the degree of polymerization of the ethylene oxide is preferably 10 to 100, more preferably 20 to 80, particularly preferably 40 to 70 and most preferably 60. Specific examples of polyoxyethylene hydrogenated castor oils include polyoxyethylene (10) hydrogenated castor oil, polyoxyethylene (40) hydrogenated castor oil, polyoxyethylene (50) hydrogenated castor oil and polyoxyethylene (60) hydrogenated castor oil.

Various polyoxyethylene castor oils having different degrees of polymerization of ethylene oxide can be used for the polyoxyethylene castor oil, and the degree of polymerization of the ethylene oxide is preferably 5 to 100, more preferably 20 to 50, particularly preferably 30 to 40 and most preferably 35. Specific examples of polyoxyethylene castor oils include Polyoxyl 5 castor oil, Polyoxyl 9 castor oil, Polyoxyl 15 castor oil, Polyoxyl 35 castor oil and Polyoxyl 40 castor oil.

Examples of polyoxyethylene polyoxypropylene glycols include polyoxyethylene (160) polyoxypropylene (30) glycol, polyoxyethylene (42) polyoxypropylene (67) glycol, polyoxyethylene (54) polyoxypropylene (39) glycol, polyoxyethylene (196) polyoxypropylene (67) glycol and polyoxyethylene (20) polyoxypropylene (20) glycol.

Examples of sucrose fatty acid esters include sucrose stearate.

Vitamin E-TPGS is also called tocopherol polyethylene glycol 1,000 succinate.

When a surfactant is incorporated into the ophthalmic depot preparation of the present invention, the amount of the surfactant can be appropriately adjusted depending on the type or the like of the surfactant, and the amount of the surfactant is preferably 0.001% (w/v) to 10% (w/v), more preferably 0.01% (w/v) to 5% (w/v), still more preferably 0.05% (w/v) to 3% (w/v) and most preferably 0.1% (w/v) to 2% (w/v).

A buffer able to be used as a pharmaceutical additive can be incorporated in the ophthalmic depot preparation of the present invention. Examples of buffers include phosphoric acid or salts thereof, boric acid or salts thereof, citric acid or salts thereof, acetic acid or salts thereof, carbonic acid or salts thereof, tartaric acid or salts thereof, ε-aminocaproic acid or salts thereof and trometamol. Examples of phosphates include sodium phosphate, sodium dihydrogen phosphate, di sodium hydrogen phosphate, potassium phosphate, potassium dihydrogen phosphate and dipotassium hydrogen phosphate, examples of borates include borax, sodium borate and potassium borate, examples of citrates include sodium citrate and disodium citrate, examples of acetates include sodium acetate and potassium acetate, examples of carbonates include sodium carbonate and sodium bicarbonate, and examples of tartrates include sodium tartrate and potassium tartrate.

When a buffering agent is incorporated into the ophthalmic depot preparation of the present invention, the amount of the buffering agent can be appropriately adjusted depending on the type or the like of the buffering agent, and the amount of the buffering agent is preferably 0.001% (w/v) to 10% (w/v), more preferably 0.01% (w/v) to 5% (w/v), still more preferably 0.05% (w/v) to 3% (w/v) and most preferably 0.1% (w/v) to 2% (w/v).

A tonicity agent able to be used as a pharmaceutical additive can be suitably incorporated in the ophthalmic depot preparation of the present invention. Examples of tonicity agents include ionic tonicity agents and nonionic tonicity agents. Examples of ionic tonicity agents include sodium chloride, potassium chloride, calcium chloride and magnesium chloride, and examples of nonionic tonicity agents include glycerin, propylene glycol, sorbitol and mannitol.

When a tonicity agent is incorporated into the ophthalmic depot preparation of the present invention, the amount of the tonicity agent can be appropriately adjusted depending on the type or the like of the tonicity agent, and the amount of the tonicity agent is preferably 0.001% (w/v) to 10% (w/v), more preferably 0.01% (w/v) to 5% (w/v), still more preferably 0.05% (w/v) to 3% (w/v) and most preferably 0.1% (w/v) to 2% (w/v).

A stabilizer able to be used as a pharmaceutical additive can be suitably incorporated in the ophthalmic depot preparation of the present invention. Examples of stabilizers include edetic acid, sodium edetate and sodium citrate.

When a stabilizer is incorporated into the ophthalmic depot preparation of the present invention, the amount of the stabilizer can be appropriately adjusted depending on the type or the like of the stabilizer, and the amount of the stabilizer is preferably 0.001% (w/v) to 10% (w/v), more preferably 0.01% (w/v) to 5% (w/v), still more preferably 0.05% (w/v) to 3% (w/v) and most preferably 0.1% (w/v) to 2% (w/v).

A preservative able to be used as a pharmaceutical additive can be suitably incorporated in the ophthalmic depot preparation of the present invention. Examples of preservatives include benzalkonium chloride, benzalkonium bromide, benzethonium chloride, sorbic acid, potassium sorbate, methyl paraoxybenzoate, propyl paraoxybenzoate and chlorobutanol.

When a preservative is incorporated into the ophthalmic depot preparation of the present invention, the amount of the preservative can be appropriately adjusted depending on the type or the like of the preservative, and the amount of the preservative is preferably 0.0001% (w/v) to 10% (w/v), more preferably 0.001% (w/v) to 5% (w/v), still more preferably 0.005% (w/v) to 3% (w/v) and most preferably 0.01% (w/v) to 2% (w/v).

An antioxidant able to be used as a pharmaceutical additive can be suitably incorporated in the ophthalmic depot preparation of the present invention. Examples of antioxidants include ascorbic acid, tocopherol, dibutylhydroxytoluene, butylhydroxyanisole, sodium erythorbate, propyl gallate and sodium sulfite or derivatives thereof, from the viewpoint of higher degree of stabilization of the drug (for example, (2-[[[2-[(hydroxyacetyl)amino]-4-pyridinyl]methyl]thio]-N-[4-(trifluoromethoxy)phenyl]-3-pyridinecarboxamide) or a salt thereof), tocopherol or derivatives thereof are particularly preferred. Examples of tocopherol and derivatives thereof include vitamin E, α-tocopherol, β-tocopherol, γ-tocopherol, δ-tocopherol, and their acetic esters, succinic esters, and their d isomer, l isomer, dl isomers.

When an antioxidant is incorporated into the ophthalmic depot preparation of the present invention, the amount of the antioxidant can be appropriately adjusted depending on the type or the like of the antioxidant, and the amount of the antioxidant is preferably 0.001% (w/v) to 10% (w/v), more preferably 0.01% (w/v) to 5% (w/v), still more preferably 0.05% (w/v) to 3% (w/v) and most preferably 0.1% (w/v) to 2% (w/v).

A high molecular weight polymer able to be used as a pharmaceutical additive can be suitably incorporated in the ophthalmic depot preparation of the present invention. Examples of high molecular weight polymers include methyl cellulose, ethyl cellulose, hydroxymethyl cellulose, hydroxyethyl cellulose, hydroxypropyl cellulose, hydroxyethyl methyl cellulose, hydroxypropyl methyl cellulose, carboxymethyl cellulose, sodium carboxymethyl cellulose, hydroxypropyl methyl cellulose acetate succinate, hydroxypropyl methyl cellulose phthalate, carboxymethylethyl cellulose, cellulose acetate phthalate, polyvinylpyrrolidone, polyvinyl alcohol, carboxyvinyl polymer and polyethylene glycol.

When a high molecular weight polymer is incorporated into the ophthalmic depot preparation of the present invention, the amount of the high molecular weight polymer can be appropriately adjusted depending on the type or the like of the high molecular weight polymer, and the amount of the high molecular weight polymer is preferably 0.001% (w/v) to 10% (w/v), more preferably 0.01% (w/v) to 5% (w/v), still more preferably 0.05% (w/v) to 3% (w/v) and most preferably 0.1% (w/v) to 2% (w/v).

A solvent able to be used as a pharmaceutical additive can be suitably incorporated in the ophthalmic depot preparation of the present invention. Examples of solvents include N-methylpyrrolidone, N,N-dimethylacetoamide and ethanol.

When a solvent is incorporated into the ophthalmic depot preparation of the present invention, the amount of the solvent can be appropriately adjusted depending on the type or the like of the solvent, and the amount of the solvent is preferably 0.1% (w/v) to 20% (w/v), more preferably 0.5% (w/v) to 15% (w/v), still more preferably 1% (w/v) to 10% (w/v) and most preferably 2% (w/v) to 5% (w/v).

A specific mode of the ophthalmic depot preparation of the present invention is an ophthalmic depot preparation substantially containing only the compound represented by formula (1) or a salt thereof, benzyl benzoate and polyethylene glycol.

Another specific mode of the ophthalmic depot preparation of the present invention is an ophthalmic depot preparation substantially containing only the compound represented by formula (1) or a salt thereof, benzyl benzoate and dimethylsulfoxide.

Another specific mode of the ophthalmic depot preparation of the present invention is an ophthalmic depot preparation substantially containing only the compound represented by formula (1) or a salt thereof, benzyl benzoate, polyethylene glycol and tocopherol or derivatives thereof.

Another specific mode of the ophthalmic depot preparation of the present invention is an ophthalmic depot preparation substantially containing only the compound represented by formula (1) or a salt thereof, benzyl benzoate, dimethylsulfoxide and tocopherol or derivatives thereof.

Another specific mode of the ophthalmic depot preparation of the present invention is an ophthalmic depot preparation substantially containing only the compound represented by formula (2) of a salt thereof, benzyl benzoate and polyethylene glycol.

Another specific mode of the ophthalmic depot preparation of the present invention is an ophthalmic depot preparation substantially containing only the compound represented by general formula (2) or a salt thereof, benzyl benzoate and dimethylsulfoxide.

Another specific mode of the ophthalmic depot preparation of the present invention is an ophthalmic depot preparation substantially containing only the compound represented by formula (2) of a salt thereof, benzyl benzoate, polyethylene glycol and tocopherol or derivatives thereof.

Another specific mode of the ophthalmic depot preparation of the present invention is an ophthalmic depot preparation substantially containing only the compound represented by formula (2) of a salt thereof, benzyl benzoate, dimethylsulfoxide and tocopherol or derivatives thereof.

The ophthalmic depot preparation of the present invention can be administered orally or parenterally. There are no particular limitations on the dosage form of the ophthalmic depot preparation of the present invention provided it is able to be used as a pharmaceutical. Examples of dosage forms include oral preparations such as liquids and suspensions and parenteral forms such as injections, transfusion fluids, nasal drops, ear drops and eye drops. Examples preferably include ophthalmic injections and eye drops, more preferably ophthalmic injections, and most preferably injections for administration into the vitreous body, anterior chamber or subconjunctival administration. These dosage forms can be produced in accordance with ordinary methods in the relevant technical field.

The ophthalmic depot preparation of the present invention can be suitably administered according to the dosage form thereof. For example, in the case of an ophthalmic injection, the ophthalmic depot preparation of the present invention can be administered into the vitreous body, in the vicinity of the posterior sclera, around the orbit or between the sclera and conjunctiva. For example, in the case of administering an ophthalmic injection into the vitreous body or anterior chamber, although there are no particular limitations on the dosage provided it is an amount sufficient for demonstrating a desired pharmacological effect, the dosage is preferably 1 μL to 100 μL, more preferably 5 μL to 70 μL, even more preferably 10 μL to 60 μL, particularly preferably 20 μL to 50 μL and most preferably 20 μL, 25 μL, 30 μL, 35 μL, 40 μL, 45 μL or 50 μL per administration. In the case of administering an ophthalmic injection subconjunctivally, although there are no particular limitations on the dosage provided it is an amount sufficient for demonstrating a desired pharmacological effect, the dosage is preferably 10 μL to 1,000 μL, more preferably 20 μL to 800 μL, even more preferably 50 μL to 700 μL, particularly preferably 100 μL to 500 μL and most preferably 100 μL, 200 μL, 300 μL, 400 μL or 500 μL per administration. The dosage of the drug is preferably 0.001 mg/eye to 30 mg/eye, more preferably 0.01 mg/eye to 10 mg/eye, even more preferably 0.1 mg/eye to 5 mg/eye, particularly preferably 0.2 mg/eye to 1.6 mg/eye and most preferably 0.2 mg/eye, 0.3 mg/eye, 0.4 mg/eye, 0.5 mg/eye, 0.6 mg/eye, 0.7 mg/eye, 0.8 mg/eye, 1 mg/eye, 1.2 mg/eye, 1.4 mg/eye or 1.6 mg/eye.

In the case of consecutively administering the ophthalmic depot preparation of the present invention into the vitreous body or anterior chamber, although there are no particular limitations on administration interval provided it is an amount sufficient for demonstrating a desired pharmacological effect, the ophthalmic depot preparation of the present invention is preferably administered at an interval of once per week to once every three years, more preferably administered at an interval of once per week, once every two weeks, once every month, once every two months, once every three months, once every four months, once every five months, once every six months, once per year, once every two years or once every three years, and most preferably administered at an interval of once every two months, once every three months, once every four months, once every five months, once every six months or once per year. In addition, the administration interval can be suitably changed.

The ophthalmic depot preparation of the present invention is useful as a pharmaceutical, and can be used as a prophylactic or therapeutic of eye diseases such as age-related macular degeneration, diabetic retinopathy, retinopathy of prematurity, retinal vein occlusion, retinal artery occlusion, polypoidal choroidal vasculopathy, retinal angiomatous proliferation, myopic choroidal neovascularization, diabetic macular edema, ocular tumor, radiation retinopathy, rubeosis iridis, neovascular glaucoma, proliferative vitreoretinopathy (PVR), primary open-angle glaucoma, secondary open-angle glaucoma, normal tension glaucoma, hypersecretion glaucoma, primary closed-angle glaucoma, secondary closed-angle glaucoma, plateau iris glaucoma, combined mechanism glaucoma, developmental glaucoma, steroid glaucoma, exfoliation glaucoma, amyloidotic glaucoma, neovascular glaucoma, malignant glaucoma, capsular glaucoma, plateau iris syndrome and high tension glaucoma. The ophthalmic depot preparation of the present invention can more preferably be used as a prophylactic or therapeutic of eye diseases such as age-related macular degeneration, diabetic retinopathy, primary open-angle glaucoma, normal tension glaucoma, primary closed-angle glaucoma and high tension glaucoma.

The ophthalmic depot preparation of the present invention can be contained in a container used for pharmaceuticals, for example, a hermetic container, especially an ampule, vial, syringe or the like. There is no particular limitation with respect to the container in which the ophthalmic depot preparation of the present invention is contained. Examples of such containers include those made of a cycloolefin polymer, glass, polyolefin such as polyethylene and polypropylene, polycarbonate or the like. From the viewpoint of the effect of the ophthalmic depot preparation to the stability of the container, use of a syringe made of a cycloolefin polymer, polypropylene or glass is preferred.

The ophthalmic depot preparation of the present invention can be stored at the temperature of −10 to 30° C., preferably −5 to 30° C., more preferably 0 to 30° C., for long-term, more than 6 months, preferably more than 1 year, more preferably 2 years, most preferably 3 years. The remaining ratio of the drug in the ophthalmic depot preparation of the present invention during long-term storage is preferably 90 to 100%, more preferably 95 to 100% and most preferably 98 to 100%.

The above explanation of the ophthalmic depot preparation of the present invention is applied to the method of the present invention for stabilizing the drug in the ophthalmic depot preparation.

The method of the present invention for stabilizing the drug in the ophthalmic depot preparation is a method in which a drug contained in an ophthalmic depot preparation is stabilized by incorporating tocopherol or derivatives thereof in the preparation, the preparation comprising:

benzyl benzoate and/or benzyl alcohol, and polyethylene glycol and/or dimethylsulfoxide, wherein, the volume ratio of benzyl benzoate and/or benzyl alcohol to polyethylene glycol and/or dimethylsulfoxide in the ophthalmic depot preparation is 75:25 to 25:75, and the total amount of benzyl benzoate and/or benzyl alcohol and polyethylene glycol and/or dimethylsulfoxide contained is 50% (w/w) or more.

Although the following indicates preparation examples and test examples, these are intended to facilitate a better understanding of the present invention, and do not limit the scope of the present invention.

PREPARATION EXAMPLES

The following indicates typical preparation examples of the present invention.

PREPARATION EXAMPLE 1

| | |
|---|---|
| Drug | 4 g |
| Benzyl benzoate | 45 g |
| PEG400 | 55 g |

PREPARATION EXAMPLE 2

| | |
|---|---|
| Drug | 4 g |
| Benzyl benzoate | 40 g |
| PEG400 | 60 g |

PREPARATION EXAMPLE 3

| | |
|---|---|
| Drug | 4 g |
| Benzyl benzoate | 45 g |
| Dimethylsulfoxide | 55 g |

PREPARATION EXAMPLE 4

| | |
|---|---|
| Drug | 4 g |
| Benzyl benzoate | 40 g |
| Dimethylsulfoxide | 60 g |

PREPARATION EXAMPLE 5

| | |
|---|---|
| Drug | 4 g |
| Benzyl benzoate | 40 g |
| PEG400 | 50 g |
| Dimethylsulfoxide | 10 g |

PREPARATION EXAMPLE 6

| | |
|---|---|
| Drug | 4 g |
| Benzyl alcohol | 45 g |
| PEG400 | 55 g |

PREPARATION EXAMPLE 7

| | |
|---|---|
| Drug | 4 g |
| Benzyl alcohol | 40 g |
| PEG400 | 60 g |

PREPARATION EXAMPLE 8

| | |
|---|---|
| Drug | 4 g |
| Benzyl alcohol | 45 g |
| Dimethylsulfoxide | 55 g |

PREPARATION EXAMPLE 9

| | |
|---|---|
| Drug | 4 g |
| Benzyl alcohol | 40 g |
| Dimethylsulfoxide | 60 g |

PREPARATION EXAMPLE 10

| | |
|---|---|
| Drug | 4 g |
| Benzyl alcohol | 40 g |
| PEG400 | 50 g |
| Dimethylsulfoxide | 10 g |

PREPARATION EXAMPLE 11

| | |
|---|---|
| Drug | 4 g |
| Benzyl benzoate | 45 g |
| PEG400 | 55 g |
| Tocopherol | 0.01 g |

PREPARATION EXAMPLE 12

| | |
|---|---|
| Drug | 4 g |
| Benzyl benzoate | 45 g |
| PEG400 | 55 g |
| Tocopherol | 0.1 g |

PREPARATION EXAMPLE 13

| | |
|---|---|
| Drug | 4 g |
| Benzyl benzoate | 45 g |
| PEG400 | 55 g |
| Tocopherol | 0.5 g |

Furthermore, the incorporated amounts of the drug, benzyl benzoate, benzyl alcohol, polyethylene glycol and dimethylsulfoxide in the aforementioned Preparation Examples 1 to 13 can be suitably adjusted to obtain a desired composition.

EXAMPLES

1. Depot Formation Evaluation Test (1)
Depot formation of the ophthalmic depot preparation of the present invention not containing a drug was evaluated.
1-1. Preparation of Test Preparations
300 µL of polyethylene glycol 400 (Croda) and 700 µL of benzyl benzoate (Sigma-Aldrich) were mixed and stirred to prepare the preparation of Example 1.
The preparations of Example 2, Example 3 and Comparative Example 1 shown in Table 1 were prepared using the same method as the preparation method of Example 1.
1-2. Test Method
5 mL of physiological saline were placed in a glass vial. 50 µL of a test preparation were injected into the physiological saline using a 30 G injection needle and Hamilton syringe. Following injection, the presence or absence of the formation of a depot by the test preparation was confirmed visually. In addition, similar tests were carried out using 1% and 2% aqueous hypromellose solutions instead of physiological saline.
1-3. Test Results and Discussion
The test results are shown in Table 1.

TABLE 1

| | | Example 1 | Example 2 | Example 3 | Comparative Example 1 |
|---|---|---|---|---|---|
| | Benzyl benzoate | 700 µL | 500 µL | 300 µL | 100 µL |
| | PEG400 | 300 µL | 500 µL | 700 µL | 900 µL |
| Depot formation | Physiological saline | ○ | ○ | ○ | X |
| | 1% aqueous hypromellose solution | ○ | ○ | ○ | X |

TABLE 1-continued

|  | Example 1 | Example 2 | Example 3 | Comparative Example 1 |
|---|---|---|---|---|
| 2% aqueous hypromellose solution | ○ | ○ | ○ | ○ |

○: Spherical depot formed
X: Depot not formed

TABLE 2

|  |  | Example 4 | Example 5 | Example 6 | Comparative Example 2 |
|---|---|---|---|---|---|
|  | Benzyl benzoate | 700 μL | 500 μL | 300 μL | 100 μL |
|  | PEG200 | 300 μL | 500 μL | 700 μL | 900 μL |
| Depot formation | Physiological saline | ○ | ○ | ○ | X |
|  | 1% aqueous hypromellose solution | ○ | ○ | ○ | X |
|  | 2% aqueous hypromellose solution | ○ | ○ | ○ | ○ |

○: Spherical depot formed
X: Depot not formed

TABLE 3

|  |  | Example 7 | Example 8 | Example 9 | Comparative Example 3 |
|---|---|---|---|---|---|
|  | Benzyl benzoate | 700 μL | 500 μL | 300 μL | 100 μL |
|  | PEG1000 | 300 μL | 500 μL | 700 μL | 900 μL |
| Depot formation | Physiological saline | ○ | ○ | ○ | — |
|  | 1% aqueous hypromellose solution | ○ | ○ | ○ | — |
|  | 2% aqueous hypromellose solution | ○ | ○ | ○ | — |

○: Spherical depot formed
—: Solidified after preparation prepared

TABLE 4

|  |  | Example 10 | Example 11 | Comparative Example 4 |
|---|---|---|---|---|
|  | Benzyl benzoate | 500 μL | 300 μL | 100 μL |
|  | DMSO | 500 μL | 700 μL | 900 μL |
| Depot formation | Physiological saline | ○ | ○ | X |
|  | 1% aqueous hypromellose solution | ○ | ○ | X |
|  | 2% aqueous hypromellose solution | ○ | ○ | ○ |

○: Spherical depot formed
X: Depot not formed

As indicated in Tables 1 to 4, the preparations of Examples 1 to 11 formed depots of similar spherical shapes even after having been injected into solutions having different viscosities. On the other hand, although the preparations of Comparative Examples 1, 2 and 4 formed spherical depots in 2% aqueous hypromellose solution, they did not form depots in physiological saline and 1% aqueous hypromellose solution. In addition, since the preparation of Comparative Example 3 solidified following preparation, it was unable to be injected with a syringe. On the basis of the above, the ophthalmic depot preparation of the present invention was confirmed to form similar spherical depots regardless of the administration site or conditions around that site.

2. Depot Formation Evaluation Test (2) Depot formation of the ophthalmic depot preparation of the present invention that contained a drug was evaluated.

2-1. Preparation of Test Preparations

The compound represented by formula (2) (2-[[[2-[(hydroxyacetyl)amino]-4-pyridinyl]methyl]thio]-N-[4-(trifluoromethoxy)phenyl]-3-pyridinecarboxamide, hereinafter to also be referred to as Compound A) was prepared according to the method described in U.S. Unexamined Patent Application Publication No. 2007/0149574. 2.75 mL of polyethylene glycol 400 (Croda) were added to 0.16 g of Compound A and stirred and after the Compound A was dissolved, 2.25 mL of benzyl benzoate (Sigma-Aldrich) were added and stirred to prepare the preparation of Example 12.

The preparations of Example 13, Example 14 and Comparative Example 5 shown in Table 5 were prepared using the same method as the preparation method of Example 12.

2-2. Test Method 5 mL of physiological saline were placed in a glass vial. 50 μL of a test preparation were injected into the physiological saline using a 30 G injection needle and Hamilton syringe. Following injection, the presence or absence of the formation of a depot by the test preparation was confirmed visually. In addition, similar tests were carried out using 1% and 2% aqueous hypromellose solutions instead of physiological saline.

2-3. Test Results and Discussion

The test results are shown in Table 5.

TABLE 5

|  |  | Example 12 | Example 13 | Example 14 | Comparative Example 5 |
|---|---|---|---|---|---|
|  | Compound A | 0.16 g | 0.16 g | 15 mg | 0.16 g |
|  | Benzyl benzoate | 2.25 mL | 2.25 mL | — | — |
|  | Benzyl alcohol | — | — | 0.25 mL | — |
|  | PEG400 | 2.75 mL | — | 0.25 mL | 5 mL |
|  | Dimethylsulfoxide | — | 2.75 mL | — | — |
| Depot formation | Physiological saline | ○ | ○ | ○ | X |
|  | 1% aqueous hypromellose solution | ○ | ○ | ○ | X |
|  | 2% aqueous hypromellose solution | ○ | ○ | ○ | ○ |

○: Spherical depot formed
X: Depot not formed

As shown in Table 5, the preparations of Examples 12 to 14 formed similar spherical depots even after having been injected into solutions having different viscosities. On the other hand, although the preparation of Comparative Example 5 formed a spherical depot in 2% aqueous hypromellose solution, it did not form a depot in physiological saline and 1% aqueous hypromellose solution. On the basis of the above, the ophthalmic depot preparation of the present invention was confirmed to form similar spherical depots regardless of the administration site or conditions around that site.

3. Depot Formation Evaluation Test (3)

Depot formation of the ophthalmic depot preparation of the present invention that contained a drug was evaluated.

3-1. Preparation of Test Preparations

The preparations of Examples 15 to 21 shown in Table 6 were prepared using the same method as the preparation method of Example 12.

3-2. Test Method 5 mL of physiological saline were placed in a glass vial. 50 µL of a test preparation were injected into the physiological saline using a 30 G injection needle and Hamilton syringe. Following injection, the presence or absence of the formation of a depot by the test preparation was confirmed visually.

3-3. Test Results and Discussion

The test results are shown in Table 6.

of the above, the ophthalmic depot preparation of the present invention was confirmed to form similar spherical depots regardless of the administration site or conditions around that site.

4. Drug Sustained Release Evaluation Test

Drug retention rates were confirmed in depots formed by the ophthalmic depot preparation of the present invention that contained a drug.

4-1. Preparation of Test Preparations

The preparations of Examples 22 to 25 and Comparative Example 6 having the composition ratios shown in Table 7 were prepared using the same method as the preparation method of Example 12.

4-2. Test Method 5 mL of physiological saline were placed in a glass vial. 20 µL or 50 µL of a test preparation were injected into the physiological saline using a 30 G injection needle and Hamilton syringe. About 1 hour later, the depot formed following injection was recovered and the amounts of Compound A in the depot and in the residual liquid were quantified using high-performance liquid chromatography (HPLC) to calculate the retention rate (%) of Compound A in the depot. In addition, similar tests were carried out for Example 23 and Comparative Example 6 using 1% and 2% aqueous hypromellose solutions instead of physiological saline.

4-3. Test Results and Discussion

The results of the tests consisting of injection into physiological saline are shown in Table 7, the results of the tests

TABLE 6

|  | Example 15 | Example 16 | Example 17 | Example 18 | Example 19 | Example 20 | Example 21 |
|---|---|---|---|---|---|---|---|
| Compound A | 12.5 mg | 12.5 mg | 12.5 mg | 12.5 mg | 12.5 mg | 80 mg | 80 mg |
| Benzyl benzoate | 214 µL | 333 µL | 500 µL | 750 µL | 1167 µL | 600 µL | 700 µL |
| PEG400 | 500 µL | 500 µL | 500 µL | 500 µL | 500 µL | — | — |
| Dimethylsulfoxide | — | — | — | — | — | 400 µL | 300 µL |
| Depot formation Physiological saline | ○ | ○ | ○ | ○ | ○ | ○ | ○ |

○: Spherical depot formed

As shown in Table 6, differing from the preparation of Comparative Example 5 described above, the preparations of Examples 15 to 21 formed similar spherical depots after having been injected into physiological saline. On the basis consisting of injection into 1% aqueous hypromellose solution are shown in Table 8, and the results of the test consisting of injection into 2% aqueous hypromellose solution are shown in Table 9.

TABLE 7

|  |  | Example 22 | Example 23 | Example 24 | Example 25 | Comparative Example 6 |
|---|---|---|---|---|---|---|
|  | Compound A | 2.5 g | 2.5 g | 2.5 g | 2.5 g | 2.5 g |
|  | Benzyl benzoate | 70 mL | 55 mL | 70 mL | 55 mL | — |
|  | PEG400 | 30 mL | 45 mL | — | 40 mL | 100 mL |
|  | Dimethylsulfoxide | — | — | 30 mL | — | — |
|  | dl-α-Tocopherol | — | — | — | 5 mL | — |
| Administration of 50 μL | Depot formation | ○ | ○ | ○ | ○ | X |
|  | Concentration of Compound A in depot (mg/mL) | 23.71 | 21.65 | 24.96 | 22.24 | 0.01 |
|  | Concentration of Compound A in residual liquid (mg/mL) | 1.30 | 0.79 | 0.48 | 0.03 | 25.23 |
|  | Retention rate of Compound A in depot | 94.8% | 96.5% | 98.1% | 99.9% | 0% |
|  | Elution rate into physiological saline | 5.2% | 3.5% | 1.9% | 0.1% | 100% |
| Administration of 20 μL | Depot formation | ○ | N.D. | ○ | N.D. | X |
|  | Concentration of Compound A in depot (mg/mL) | 22.75 |  | 23.34 |  | 0.01 |
|  | Concentration of Compound A in residual liquid (mg/mL) | 0.75 |  | 0.76 |  | 22.76 |
|  | Retention rate of Compound A in depot | 96.8% |  | 96.8% |  | 0% |
|  | Elution rate into physiological saline | 3.2% |  | 3.2% |  | 100% |

○: Spherical depot formed
X: Depot not formed
N.D.: No data

TABLE 8

|  |  | Example 23 | Comparative Example 6 |
|---|---|---|---|
|  | Compound A | 2.5 g | 2.5 g |
|  | Benzyl benzoate | 55 mL | — |
|  | PEG400 | 45 mL | 100 mL |
| Administration of 50 μL | Depot formation | ○ | X |
|  | Concentration of Compound A in depot (mg/mL) | 16.95 | 0.04 |
|  | Concentration of Compound A in residual liquid (mg/mL) | 5.08 | 24.82 |
|  | Retention rate of Compound A in depot | 76.9% | 0.2% |
|  | Elution rate into 1% aqueous hypromellose solution | 23.1% | 99.8% |

○: Spherical depot formed
X: Depot not formed

TABLE 9

|  |  | Example 23 | Comparative Example 6 |
|---|---|---|---|
|  | Compound A | 2.5 g | 2.5 g |
|  | Benzyl benzoate | 55 mL | — |
|  | PEG400 | 45 mL | 100 mL |
| Administration of 50 μL | Depot formation | ○ | ○ |
|  | Concentration of Compound A in depot (mg/mL) | 19.64 | 23.51 |
|  | Concentration of Compound A in residual liquid (mg/mL) | 0.48 | 1.36 |
|  | Retention rate of Compound A in depot | 97.6% | 94.5% |
|  | Elution rate into 2% aqueous hypromellose solution | 2.4% | 5.5% |

○: Spherical depot formed

As shown in Tables 7, 8 and 9, the preparations of Examples 22 to 25 formed similar spherical depots when injected into physiological saline, and the retention rate of Compound A in the depots was 90% or more. In addition, the preparation of Example 23 formed a similar spherical depot even after having been injected into 1% aqueous hypromellose solution and 2% aqueous hypromellose solution, and the retention rate of Compound A in the depot was 70% or more. On the other hand, the preparation of Comparative Example 6 did not form a depot even when injected into physiological saline and 1% aqueous hypromellose solution, and Compound A was released into the residual liquid without being retained in the depot. Especially, in the case of the 1% aqueous hypromellose solution, when the syringe was taken out from the 1% aqueous hypromellose solution, the preparation of Comparative Example 6 was stringy (exhibited stringiness). This fact was regarded as one of the reasons of the failure to form a spherical depot. Such stringiness was not perceived in the preparation of Examples 23 which formed a spherical depot. On the basis of the above, the ophthalmic depot preparation of the present invention was confirmed to form similar spherical depots and gradually release a drug regardless of the administration site or conditions around that site.

5. Drug Dissolution Performance Evaluation Test

The drug dissolution performance of the ophthalmic depot preparation of the present invention was examined.

5-1. Preparation of Test Preparations

400 µL of dimethylsulfoxide (Gaylord Chemical) were added to 0.08 g of Compound A, and after stirred and dissolved, 600 µL of benzyl benzoate (Sigma-Aldrich) were added, stirred and dissolved to prepare the preparation of Example 26.

Preparations of Example 27 and Comparative Examples 7 and 8 having the composition ratios shown in Table 10 were prepared using the same method as the preparation method of Example 26.

5-2. Test Method

Dissolution of the test preparations was confirmed visually.

5-3. Test Results and Discussion

The test results are shown in Table 10.

TABLE 10

|  | Example 26 | Example 27 | Comparative Example 7 | Comparative Example 8 |
|---|---|---|---|---|
| Compound A | 0.08 g | 0.08 g | 0.08 g | 0.08 g |
| Benzyl benzoate | 600 µL | 700 µL | 800 µL | 1000 µL |
| Dimethylsulfoxide | 400 µL | 300 µL | 200 µL | 0 µL |
| Solubility | ◯ | ◯ | X | X |

◯: Completely dissolved
X: Not completely dissolved

As shown in Table 10, in the preparations of Examples 26 and 27 Compound A was completely dissolved. On the other hand, in the preparations of Comparative Examples 7 and 8, Compound A was not completely dissolved. On the basis of the above, the ophthalmic depot preparation of the present invention was confirmed to be capable of adequately dissolving a drug.

6. Depot Formation Evaluation Test in an Animal

The ophthalmic depot preparation of the present invention containing a drug was administered into the vitreous of an animal and the depot formation was evaluated in vivo.

6-1. Preparation of Test Preparations 55 mL of polyethylene glycol 400 (Croda) was added to Compound A 5 g to dissolve Compound A by stirring. Preparation of Example 28 was prepared further by adding dl-α-tocopherol (Merck) 0.2 mL and then by adding benzyl benzoate (Merck) to a total volume of 100 mL. Preparation of Comparative Example 9 as shown in Table 11 was prepared using the same method as the preparation method of Example 28.

TABLE 11

|  | Example 28 | Comparative Example 9 |
|---|---|---|
| Compound A | 5 g | 5 g |
| PEG400 | 55 mL | q.s. |
| Benzyl benzoate | q.s. | — |
| dl-α-Tocopherol | 0.2 mL | — |
| Total volume | 100 mL | 100 mL |

6-2. Test Method

Test preparations were intravitreally injected into white rabbits (20 µL/eye) using a 30 gauge needle and, after 4 hours from the administration, eyes were enucleated. With respect to each of the enucleated eyes, an incision was made in the pars plana to remove the tissues of the anterior segment (such as lens, cornea and the like), and an image of the state of the depot formed in the eye was taken with a camera.

6-3. Test Results and Discussion

The test results are shown in the FIGURE.

As shown in the FIGURE, the preparation of Example 28 formed a spherical depot with a sharply defined interface between the vitreous body and depot. On the other hand, the preparation of Comparative Example 9 formed an depot with an ill-defined interface between the vitreous body and depot, and a randomly unstable shape. On the basis of the above, the ophthalmic depot preparation of the present invention was confirmed to form a spherical depot even when administered into the vitreous body.

7. Syringe Compatibility Test

The compatibility of the ophthalmic depot preparation of the present invention with various syringes was evaluated.

7-1. Preparation of a Test Preparation

A preparation of Example 29 as shown in Table 12 was prepared using the same method as the preparation method of Example 28.

TABLE 12

|  | Example 29 |
|---|---|
| PEG400 | q.s. |
| Benzyl benzoate | 50 mL |
| dl-α-Tocopherol | 0.2 mL |
| Total Volume | 100 mL |

7-2. Test Method

A 23 G injection needle was attached to the syringes shown in Table 13, and the syringe was filled with approximately 90% of the volume of syringe of the preparation of Example 29. The injection needle was replaced with a 30 G injection needle, and the cavity space formed in the injection needle was filled with the preparation. The syringe was stored at 25° C. or 60° C. for 6 hours. After 6 hours, the state of the syringe was visually observed.

7-3. Test Results and Discussion

The test results are shown in Table 13.

TABLE 13

| External Syringe material | Supplier | Temperature/Time | Results |
|---|---|---|---|
| Polycarbonate | MERIT MEDICAL (CUSTOM KIT 0.02 mL Medallion Sword Handle) | 60° C./6 hours | Cracks generated |
|  |  | 25° C./6 hours | Cracks generated |

TABLE 13-continued

| External Syringe material | Supplier | Temperature/Time | Results |
|---|---|---|---|
| Cycloolefin polymer | MERIT MEDICAL (1 mL Medallion Sword Handle) | 60° C./6 hours | No change in the syringe |
| | | 25° C./6 hours | No change in the syringe |
| Polypropylene | TOP (SENSYTEC SYRINGE) | 60° C./6 hours | No change in the syringe |
| | | 25° C./6 hours | No change in the syringe |
| Glass | Hamilton (100 μL Hamilton Syringe) | 60° C./6 hours | No change in the syringe |
| | | 25° C./6 hours | No change in the syringe |

As shown in Table 13, when the preparation of Example 29 was used in a syringe made of a cycloolefin polymer, polypropylene or glass, no change was perceived in the syringe. On the other hand, when this preparation was used in a syringe made of a polycarbonate, cracks were generated in the syringe. It was suggested that when the ophthalmic depot preparation of the present invention was stored for a long period of time in a prefilled syringe, a syringe made of a cycloolefin polymer, polypropylene or glass was more suitable than a syringe made of a polycarbonate.

8. Drug Stability Test

The stability of a drug (compound A) in the ophthalmic depot preparation of the present invention was evaluated.

8-1. Preparation of a Test Preparation 30.8 g of polyethylene glycol 400 (NOF CORPORATION) was added to Compound A 1.25 g to dissolve Compound A by stirring. Pharmaceutical composition D was prepared further by adding dl-α-tocopherol (BASF) 0.5 mL and then by adding benzyl benzoate (Sigma-Aldrich) to a total volume of 50 mL. 1.59 mL of the pharmaceutical composition was filled in a 2 mL glass vial (Wheaton, internal content 2.92 mL) and then sealed with rubber stopper to provide preparation of Example 30.

Preparation of Examples 31 to 36 as shown in Tables 14 and 15 were prepared using the same method as the preparation method of Example 30. The filling rate was calculated by the volume of pharmaceutical composition in the container/the inner volume of the container.

8-2. Test Method

With respect to each of the preparations of Examples 30 to 36, the amount of compound A contained in the preparation after the storage of 4 weeks at the temperature of 40° C. and relative humidity of 20% was determined by high-performance liquid chromatography (HPLC), and the remaining ratio of compound A was calculated.

8-3. Test Results and Discussion

The test results are shown in Tables 14 and 15.

TABLE 14

| | Example 30 | Example 31 | Example 32 | Example 33 | Example 34 |
|---|---|---|---|---|---|
| Compound A | 1.25 g | 1.25 g | 1.25 g | 1.25 g | 1.25 g |
| PEG400 | 30.8 g | 30.8 g | 30.8 g | 30.8 g | 30.8 g |
| Benzyl benzoate | q.s. | q.s. | q.s. | q.s. | q.s. |
| dl-α-tocopherol | 0.5 mL | 0.25 mL | 0.1 mL | 0.01 mL | 0.001 mL |
| Total volume | 50 mL | 50 mL | 50 mL | 50 mL | 50 mL |
| Filling ratio | 54% | 54% | 54% | 54% | 54% |
| Remaining ratio of compound A (%) (40° C./4 weeks) | 97.6 | 97.6 | 97.2 | 98.0 | 98.4 |

TABLE 15

| | Example 35 | Example 36 |
|---|---|---|
| Compound A | 0.96 g | 0.96 g |
| PEG400 | 16.5 mL | 16.5 mL |
| Benzyl benzoate | 12 mL | 13.5 mL |
| dl-α-tocopherol | 1.5 mL | — |
| Filling ratio | 54% | 54% |
| Remaining ratio of compound A (%) (40° C./4 weeks) | 98.7 | 95.4 |

As shown in Tables 14 and 15, in the preparation of Example 36 containing no dl-α-tocopherol, the remaining ratio of compound A was 95% or more, and in each of the preparations of Examples 30 to 35 each containing dl-α-tocopherol, the remaining ratio of compound A was 97% or more, which was higher than the former. On the basis of the above, it was suggested that compound A was further stabilized when tocopherol or derivatives thereof were contained in the ophthalmic depot preparation of the present invention.

The invention claimed is:

1. An ophthalmic depot preparation, consisting of:
    a drug,
    benzyl benzoate,
    polyethylene glycol and/or dimethylsulfoxide, and
    optionally an additive; wherein,
    the volume ratio of benzyl benzoate to polyethylene glycol and/or dimethylsulfoxide in the ophthalmic depot preparation is 75:25 to 25:75,
    the total amount of benzyl benzoate and polyethylene glycol and/or dimethylsulfoxide contained is 80% (w/w) or more,
    the polyethylene glycol is a polyethylene glycol selected from the group consisting of PEG100, PEG200, PEG300, PEG400 and PEG600,
    the additive is at least one additive selected from the group consisting of surfactants, buffering agents, tonicity agents, stabilizers, preservatives, antioxidants, and solvents, the antioxidant is selected from the group consisting of ascorbic acid, dibutylhydroxytoluene, butylhydroxyanisole, sodium erythorbate, propyl gallate, sodium sulfite and derivatives thereof, and said ophthalmic depot preparation is not a depot before being administered in a body, and forms a depot after being administered in a body and gradually releases the drug.

2. The ophthalmic depot preparation according to claim 1, wherein the drug is a compound represented by formula (1):

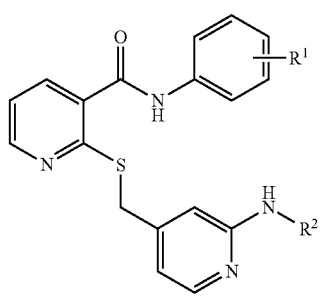

(1)

wherein,
R$^1$ represents a hydrogen atom, halogen atom, hydroxyl group, C$_{1-6}$ alkyl group, C$_{1-6}$ alkyl group substituted with one or more halogen atoms, C$_{1-6}$ alkoxy group, or C$_{1-6}$ alkoxy group substituted with one or more halogen atoms, and R$^2$ represents a hydrogen atom, C$_{1-6}$ alkyl group, C$_{1-6}$ alkylcarbonyl group, or C$_{1-6}$ alkylcarbonyl group substituted with one or more hydroxyl groups, or a salt thereof.

3. The ophthalmic depot preparation according to claim 2, wherein in the formula (1)
R$^1$ represents a C$_{1-6}$ alkoxy group or C$_{1-6}$ alkoxy group substituted with one or more halogen atoms, and
R$^2$ represents a C$_{1-6}$ alkylcarbonyl group or C$_{1-6}$ alkylcarbonyl group substituted with one or more hydroxyl groups.

4. The ophthalmic depot preparation according to claim 2, wherein in the formula (1)
R$^1$ represents a C$_{1-6}$ alkoxy group substituted with one or more halogen atoms, and
R$^2$ represents a C$_{1-6}$ alkylcarbonyl group substituted with one or more hydroxyl groups.

5. The ophthalmic depot preparation according to claim 2, wherein the compound represented by formula (1) is 2-[[[2-[(hydroxyacetyl)amino]-4-pyridinyl]methyl]thio]-N-[4-(trifluoromethoxy)phenyl]-3-pyridinecarboxamide or a salt thereof.

6. The ophthalmic depot preparation according to claim 1, wherein the polyethylene glycol is PEG400.

7. The ophthalmic depot preparation according to claim 1, wherein the volume ratio of benzyl benzoate to polyethylene glycol and/or dimethylsulfoxide is 60:40 to 35:65.

8. The ophthalmic depot preparation according to claim 1, wherein the volume ratio of benzyl benzoate to polyethylene glycol and/or dimethylsulfoxide is 50:50 to 40:60.

9. The ophthalmic depot preparation according to claim 1, wherein the total amount of benzyl benzoate and polyethylene glycol and/or dimethylsulfoxide contained is 90 to 99% (w/w).

10. The ophthalmic depot preparation according to claim 1, wherein the total amount of benzyl benzoate contained is 25% (w/w) to 60% (w/w).

11. The ophthalmic depot preparation according to claim 1, wherein the total amount of polyethylene glycol and/or dimethylsulfoxide contained is 30% (w/w) to 62% (w/w).

12. The ophthalmic depot preparation according to claim 1, which is for administration into the vitreous body or anterior chamber.

13. The ophthalmic depot preparation according to claim 1, wherein the drug is contained at 0.001% (w/v) to 30% (w/v).

14. The ophthalmic depot preparation according to claim 1, which is for treatment of an eye disease.

15. The ophthalmic depot preparation according to claim 1, which is contained in a container made of glass, cycloolefin polymer, polyolefin or polycarbonate.

16. An ophthalmic depot preparation, consisting of:
a drug,
benzyl benzoate, and
polyethylene glycol and/or dimethylsulfoxide; wherein,
the volume ratio of benzyl benzoate to polyethylene glycol and/or dimethylsulfoxide in the ophthalmic depot preparation is 75:25 to 25:75,
the total amount of benzyl benzoate and polyethylene glycol and/or dimethylsulfoxide contained is 80% (w/w) or more,
the polyethylene glycol is a polyethylene glycol selected from the group consisting of PEG100, PEG200, PEG300, PEG400 and PEG600, and
said ophthalmic depot preparation is not a depot before being administered in a body, and forms a depot after being administered in a body and gradually releases the drug.

* * * * *